United States Patent [19]

Nair et al.

[11] Patent Number: 4,540,581
[45] Date of Patent: Sep. 10, 1985

[54] TOPICAL NONSTEROIDAL ANTI-INFLAMMATORY COMPOSITIONS AND USES

[75] Inventors: Xina Nair, East Amherst, N.Y.; Davis L. Temple, Jr., Evansville, Ind.

[73] Assignee: Bristol-Myers Company, New York, N.Y.

[21] Appl. No.: 575,418

[22] Filed: Jan. 31, 1984

[51] Int. Cl.³ .................... A61K 31/18; A61K 31/24; A61K 31/40; A61K 31/235
[52] U.S. Cl. .................................. 514/415; 514/538; 514/539; 514/605
[58] Field of Search ............... 424/321, 274, 308, 309

[56] References Cited

U.S. PATENT DOCUMENTS

| | | | |
|---|---|---|---|
| 3,341,584 | 9/1967 | Larsen et al. | 260/556 |
| 3,919,424 | 11/1975 | Comer et al. | 424/316 |
| 3,993,776 | 11/1976 | Comer et al. | 424/316 |
| 4,088,756 | 5/1978 | Voorhees | 424/180 |
| 4,138,581 | 2/1979 | Minatoya et al. | 560/109 |
| 4,323,575 | 4/1982 | Jones | 424/267 |

OTHER PUBLICATIONS

Green, Br. J. Pharmac., vol. 45, pp. 322–332, (1972).
Swingle et al., Arch. Int. Pharmacodyn, vol. 254, pp. 168–176, (1981).
Jack et al., Toxicology, vol. 27, pp. 315–320, (1983).
New Drug Commentary 7(8), Issue 68, p. 23, (1980).
McGraw-Hill Dictionary of Scientific & Tech. Terms, 2nd ed., 1978, (4/18), p. 72.
Drugs of the Future, IV, 629, (1979), 5/26.
R. Seely et al., Proc. Soc. Exp. Biol. Med. 159,223, (1978), 5/23.
Temple et al., Jour. Med. Chem., vol. 19, No. 5, pp. 626–633, (1976), 5/13.
Seo et al., European J. of Pharmacology, 63,267–274, (1980), 6/5.
Riggilo et al., Proc. Soc. Exp. Biol. & Med., vol. 140, pp. 667–669, (1972).

*Primary Examiner*—Stanley J. Friedman
*Attorney, Agent, or Firm*—Richard R. Lloyd

[57] ABSTRACT

New compositions using particular $\beta_2$ agonists and vehicle materials have been prepared and are useful for producing a topical anti-inflammatory effect in mammals. The selected $\beta_2$ agonists have previously not been known to exhibit topical antiinflammatory activity. The compositions can be for example in the form of sprays, ointments, creams, gels, lotions, and suppositories, all of which are to be applied to the mammal topically, as opposed to systemically.

9 Claims, No Drawings

TOPICAL NONSTEROIDAL ANTI-INFLAMMATORY COMPOSITIONS AND USES

BACKGROUND OF THE INVENTION

This invention relates generally to anti-inflammatory, topically applied nonsteroidal compositions and to their uses and relates more specifically to such compositions having as active ingredient $\beta_2$-adrenergic agonist(s).

Applicants emphasize that although there are at least hundreds (perhaps thousands) of $\beta_2$-agonists known in the art, only salbutamol has been disclosed as having any topical anti-inflammatory activity. It is believed that no structure-to-activity relationship for predicting topical anti-inflammatory activity is known in the art at this time. The art area is very unpredictable.

Inflammation is exhibited by most skin diseases. A variety of inflammatory skin diseases and conditions (including chronic and acute types) has resulted in an ongoing search for anti-inflammatory drugs.

The introduction of steroids provided the dermatologist with a class of anti-inflammatory agents that are therapeutically active against a wide spectrum of inflammatory skin diseases. However, the effect of steroids in many inflammatory conditions, particularly in those of a chronic nature, is only palliative and requires extended use. And such extended use of steroids also results in various adverse effects, including atrophy of skin, striae, telangiectasia, steriod acne, and adrenal suppression, especially in children. Additionally, in various chronic inflammatory skin diseases, the termination of steroid therapy has led to the reappearance of inflammatory symptoms and sometimes with increased intensity. In response to the drawbacks of using steroids, over the last 20 years many new nonsteroidal anti-inflammatory agents (i.e., NSAIA) have been developed for use in various diseases, including rheumatic diseases. These compounds generally appear to be free of some of the adverse effects of steroids, especially tissue atrophy, adrenal suppression, and other less severe rebound effects.

One class of compounds included within the group of NSAIA is a group of compounds that are prostaglandin synthetase inhibitors. These materials are generally active in reducing UVB-induced erythema (i.e., erythema induced by ultraviolet light) in guinea pigs; but the materials are only slightly active or are inactive in other tests relating to dermatitis, including the croton oil and the oxazolone ear edema assays further described in the examples below. Therefore, other classes of nonsteroidal compounds with topical anti-inflammatory activity are of interest.

$\beta$ adrenergic agonists (including $\beta_1$ and $\beta_2$ agonists) are compounds which have been proposed to act through the stimulation of adenylate cyclase, resulting in the conversion of adenosine triphosphate (i.e., ATP) to cyclic 3',5',-adenosine monophosphate (i.e., C-AMP). See, for example, R. J. Brittain, et al, Adv. Drug Res. 5, 197, 1970. The walls of essentially all nucleated mammalian cells contain the enzyme adenylate cyclase, which is stimulated by various compounds including prostaglandin E and $\beta$-adrenergic drugs.

Adenylate cyclase activity has been reported to be present in human and animal epidermis. Disorders in adenylate cyclase activity and in C-AMP levels have been reported in proliferative skin diseases such as eczema, psoriasis, epidermolytic hyperkeratosis and lamellar ichthyosis.

In short, $\beta$ agonists are a class of compounds which stimulate the adrenergic system of the human body.

Materials which are classified as $\beta_1$ agonists are $\beta$ agonists which selectively react with the $\beta_1$ receptors and elicit cardiac stimulation.

Materials which are classified as $\beta_2$ agonists selectively react with the $\beta_2$ receptors which are present in the smooth muscles of the blood vessels and bronchi; these materials elicit bronchodilation and vasodilation.

In British Pat. No. 4,323,575 to G. Jones, Apr. 6, 1982, disubstituted catecholamines (which may or may not be $\beta_2$ agonists) having topical anti-inflammatory activity are disclosed.

In U.S. Pat. No. 3,341,584 to Larsen et al sulfonanilides having the general formula I are disclosed.

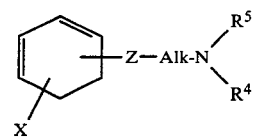

As disclosed in that patent, the sulfonanilides of formula I, wherein Z is CHOH, are pharmacologically active phenethanolamines having actions which either resemble the effects of the adrenal medullary hormones or adrenergic neurotransmitters or oppose the effects of the adrenal medullary hormones or adrenergic neurotransmitters. Alkyl and aryl-sulfonamido nuclearly substituted phenalkanolamines have useful pharmacologic effects, suiting them variously as vasopressors, vasodepressors, analgesics, bronchodilators, $\alpha$-receptor stimulants, $\beta$-receptor stimulants, $\alpha$-receptor blocking agents, $\beta$-receptor blocking agents, papaverine-like smooth muscle depressants, or anti-inflammatory agents useful in controlling or preventing anaphylaxis.

Anaphylaxis is defined in the *McGraw-Hill Dictionary of Scientific and Technical Terms*, Second Edition, 1978, as hypersensitivity following parenteral injection of an antigen, wherein local or systemic allergenic reaction occurs when the antigen is reintroduced after a time lapse. Topical is defined to be "local or designed for local application" and that term is so used in this application. Therefore, because anaphylaxis and topical inflammations are different conditions physiologically, a drug which is useful in treating one of these conditions is generally not useful in treating the other condition.

In U.S. Pat. No. 3,801,631, 2-hydroxy-5'-[1-hydroxy-2-(2-methyl-1-phenyl-2-propylamino)ethyl]methanesulfonanilide, called zinterol (which is included within the broad genus of sulfonic acid amides disclosed in U.S. Pat. No. 3,341,584 cited above) is disclosed. Zinterol was there described as a potent anorexigenic agent, as a bronchodilator, and as having analgesic activity.

In the article "Adrenergic Sulfonanilides. 4. Centrally Active $\beta$-Adrenergic Agonists", D. L. Temple et al, *Journal of Medicinal Chemistry*, Vol. 19, No. 5, Pgs. 626–633 (1976), zinterol (compound No. 43) is described as a potent anorexiant and as a narcotic antagonist.

Additionally, in U.S. Pat. No. 3,919,424 and in U.S. Pat. No. 3,993,776, further description of the uses of zinterol is given.

Salbutamol is a $\beta_2$ agonist. This material was described in R. Seely et al, *Proc. Soc. Exp. Biol. Med.* 159, 223 (1978) as being useful as a topical anti-inflammatory agent.

The synthesis of salbutamol is described in *Drugs of the Future* IV, 629 (1979). There, salbutamol is indicated as being useful as an anti-inflammatory agent when applied locally. It is further stated that salbutamol given orally in the control of asthma compares favorably with related drugs. A mechanism for the action of salbutamol is proposed. (See page 631 of the reference.)

A 1980 publication by Saiichirou Seo et al, "Inhibition of Adjuvant Arthritis by Salbutamol and Aminophylline," European J. of Pharmacology, 63, 267–274, 1980, describes inhibition of swelling in the paws of mice by injections of combinations of salbutamol and aminophylline.

Other materials showing some structural similarity to zinterol and having topical anti-inflammatory activity are disclosed in U.S. Pat. No. 4,323,575 to Jones. These materials may or may not be β-agonists and only testing would determine whether they are.

In U.S. Pat. No. 4,088,756 to Voorhees, other β-agonists which may or may not have anti-inflammatory activity are disclosed.

However, as further described below, which $\beta_2$-agonists will be effective topical anti-inflammatory agents cannot be predicted with any reasonable degree of certainty. After much experimentation, applicants found that nearly all $\beta_2$ agonists they tested for such activity were either ineffective, highly toxic, or both.

Therefore, despite what has been known in the prior art, there is a continuing need for non-steroidal anti-inflammatory drugs which exhibit consistently good anti-inflammatory activity and which are nontoxic.

SUMMARY OF THE INVENTION

An object of this invention is a material which when placed into a suitable vehicle provides a composition which when topically applied reduces the amount of topical inflammation of a mammal.

Another object of this invention is a composition in the form of an ointment, cream, lotion or other formulation to be topically applied to a mammal so as to reduce or hinder the development of skin inflammation.

A further object of this invention is a method of using a compound (or compounds, in a mixture) for the purpose of reducing topical inflammation of mammals.

The above-described objects are satisfied by the compositions of the present invention, which comprise:

(a) An amount effective to produce a topical anti-inflammatory effect of at least one compound (or pharmaceutically acceptable salt(s) or solvate(s) thereof) selected from the group consisting of compounds having the general formula II

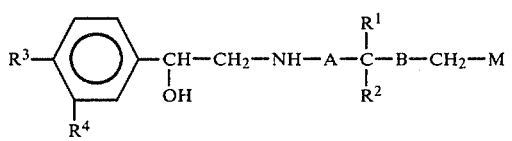

wherein $R^1$ and $R^2$ are independently H or a lower alkyl group, provided that $R^1$ and $R^2$ cannot both be H, M is either H, a phenyl group, or an indole group of formula (a)

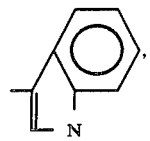

A is $(—CH_2—)_n$ which n is the integer 0, 1, or 2, and B is $(—CH_2)_m$ in which m is the integer 0, 1, or 2, $R^3$ is either

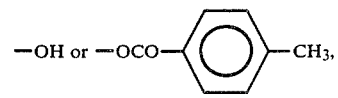

and $R^4$ is either

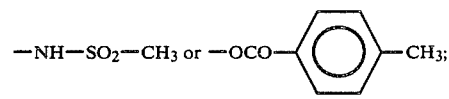

and (b) A dermatologically acceptable carrier therefor.

In a preferred aspect of the invention, $R^1$ and $R^2$ are both methyl groups and m and n are both 0. A preferred compound for use in the methods and compositions of the invention is the compound of formula II wherein n is 0, m is 0, $R_1$ is —$CH_3$, $R^2$ is —$CH_3$, M is phenyl, $R^3$ is —OH, and $R^4$ is —NH—$SO_2$—$CH_3$. This compound is known as zinterol (referred to hereinafter as compound III).

Another preferred compound for use in the methods and compositions of the invention is the compound of formula II wherein n is 0, m is 0, $R^1$ is —$CH_3$, $R^2$ is H, M is an indole group, $R^3$ is —OH, and $R^4$ is —NH—$SO_2$—$CH_3$, which compound is hereinafter referred to as Compound IV.

Yet another preferred compound for use in the methods and compositions of the invention is the compound of formula II wherein n is 0, m is 0, $R^1$ and $R^2$ are both —$CH_3$, M is an indole group, $R^3$ is —OH, and $R^4$ is —NH—$SO_2$—$CH_3$, which compound is hereinafter referred to as Compound V or azazinterol.

A still further preferred compound for use in the methods and compositions of the invention is the compound of formula II wherein n is 0, m is 0, $R^1$ and $R^2$ are both —$CH_3$, M is hydrogen, and $R^3$ and $R^4$ are both

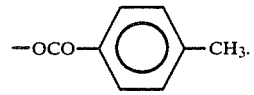

That compound is hereinafter referred to as bitolterol and is commercially available for use in treating allergies but has not been known previously to be useful for treating topical inflammations.

In another aspect of the invention, a method for reducing topical inflammation in mammals comprises: applying a compound of formula II topically to the mammal so that localized (as opposed to systemic) activity against topical inflammation results.

Further, according to the invention, a composition to be topically applied to reduce the amount of topical inflammation of mammals comprises at least one compound of formula II present in a nontoxic amount sufficient to reduce inflammation and present in a pharmaceutically acceptable carrier material or materials, wherein A, B, $R^1$, $R^2$, $R^3$, $R^4$ and M are as described above.

In another preferred aspect of the invention, a composition to be topically applied comprises at least one compound selected from the group consisting of zinterol, compound IV, compound V, and bitolterol, at least one compound of which is present in an amount sufficient to reduce inflammation but insufficient to be toxic and present in a pharmaceutically acceptable carrier.

It is emphasized that the term "topical" as used throughout this document means local or designed for local application to produce a local effect with preferably no concomitant systemic effect. Thus, the compounds to be used in the methods and compositions of the invention can be applied in any of a variety of ways, provided that they are not injected or swallowed. They can be applied, for example, cutaneously, nasally, vaginally, rectally, otically, and buccally. They will be used with a dermatogically acceptable vehicle preferably chosen such that systemic absorption of the active ingredient is hindered or reduced.

DESCRIPTION OF THE PREFERRED EMBODIMENTS

The compound(s) which are to be placed into a vehicle so as to provide a composition(s) suitable for topical use as an anti-inflammatory preparation(s) in mammals are the compounds of formula II, recited above, (or pharmaceutically acceptable salts and solvates thereof), wherein M is either a phenyl group, or an indole group or hydrogen, wherein A is $(-CH_2-)_n$ and wherein n equals 0, 1, or 2; wherein B is $(-CH_2)_m$ and wherein m is 0, 1, or 2; wherein $R^1$ and $R^2$ are independently H or a lower alkyl group, provided that $R^1$ and $R^2$ cannot both be H; wherein $R^3$ is either —OH or

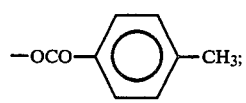

and wherein $R^4$ is either

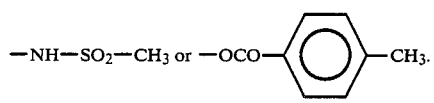

Applicants wish to emphasize that they tested many $\beta_2$ adrenergic agonists (all of which are analogs of zinterol). Of approximately 45 such compounds, only four had consistently high topical anti-inflammatory activity without apparent toxicity in tests which are described in the examples below. The remainder of the compounds, on the other hand, exhibited either toxicity when applied topically to the test animals, ineffective and/or inconsistent anti-inflammatory activity, or both.

The compound(s) to be placed into a vehicle so as to provide a composition suitable for topical use as an anti-inflammatory preparation in mammals are prepared in the following manner.

The preparation of zinterol is described in detail in U.S. Pat. No. 3,801,631 to William T. Comer et al, "2'-hydroxy-5'-[1-hydroxy-2-(2-methyl-1-phenyl-2-propylamino)ethyl]methanesulfonanilide and Its Salts"; and that patent is hereby incorporated herein by reference.

The following procedure can be used for preparation of compounds IV and V:

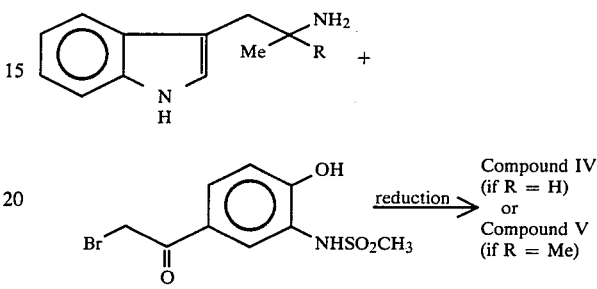

This process comprises alkylation of the phenolic bromoketone by the appropriate indolylalkylamine followed by reduction of the carbonyl group to a secondary alcohol. In practice, the phenolic OH group is protected during the nucleophilic displacement reaction. This is done to prevent participation by the phenolic group in nucleophilic attack of its own thereby giving unwanted ether byproducts. Generally, the protection is done via a benzyl group which is subsequently removed by catalytic reduction.

As used herein, Me stands for a methyl group. A detailed description of the preparation of compounds IV and V is given in pending U.S. application having Ser. No. 471,976 filed on Mar. 4, 1983; and the contents of that patent application are hereby incorporated herein by reference.

The preparation of bitolterol is discussed in U.S. Pat. No. 4,138,581; and that discussion is hereby incorporated herein by reference.

For medicinal use, the pharmaceutically acceptable solvates and salts are those complexes in which the solvent, metal cation or acid anion does not contribute significantly to toxicity or pharmacological activity of the organic drug ion. Examples of metal salts include the sodium, potassium, calcium, magnesium, aluminum and zinc salts. Metal and acid addition salts are obtained, respectively, either by reaction of the selected compound with a suitable metallic base to form a metal salt or with an organic or inorganic acid to form an acid addition salt, preferably by contact in solution, or by any of the standard methods detailed in the literature and available to any practitioner skilled in the art. Examples of useful organic acids are carboxylic acids such as maleic acid, acetic acid, tartaric acid, propionic acid, fumaric acid, isethionic acid, succinic acid, pamoic acid, cyclamic acid, pavalic acid, and the like. Useful inorganic acids are hydrohalide acids (such as HCl, HBr, HI), sulfuric acid, phosphoric acid, and the like.

Solvates as used herein are complexes comprising an organic drum molecule and a solvent moiety of formula ROH, wherein R most commonly is hydrogen or a $C_1$ or $C_4$ alkyl group. The most common solvate is the hydrate.

The compounds recited above which are to be placed into a vehicle so as to provide compositions suitable for topical use as anti-inflammatory preparations in mammals can be placed into the following vehicles. The resulting mixtures are pharmaceutical preparations of the invention. The vehicle can be any nontoxic material or mixture of materials which is suitable for use in preparing pharmaceutically acceptable ointments, salves, lotions, sprays, suppositories and other similar medicaments. The vehicle, additionally, will be chosen so that it preferably hinders or reduces systemic absorption of the active material(s) and it should not react with the active ingredient(s) described above. Additionally, the active ingredient(s) should be both soluble in the vehicle and should be released by the vehicle topically. Furthermore, the mixtures so formed will preferably be stable over an extended period of time, for example on the order of months or years.

The active ingredient(s) will generally be dissolved into a component of the vehicle. For example, zinterol hydrochloride is both water soluble and soluble at least to some extent in various organic materials. For topical applications to the skin, because there is both an aqueous phase and a nonaqueous phase in the skin, both water soluble and oil soluble portions of the vehicle will permeate the skin. However, for topical use, one would use some organic phase in the vehicle (for example, petrolatum or mineral oil).

Vehicles for carrying active ingredients into the skin, for example, creams, lotions, gels, ointments, suppositories, and sprays, as well as methods of preparation thereof, are well known in the art. In the present invention, at least one active ingredient will be dissolved in a portion of the vehicle in which it is soluble, and the resulting mixture will then be mixed in any suitable way with the remaining ingredients of the vehicle.

The relative amount of vehicle to be mixed with active ingredient(s) (i.e., with the compounds described above) in forming the mixtures of the invention will be selected depending upon the solubility of the active ingredient(s) in the vehicle. However, it is believed that the optimal concentration is generally the saturation point. For zinterol hydrochloride, however, the optimal concentration thereof in a cream vehicle was found to be 0.2 w/v percent, although up to 0.7 w/v percent thereof will dissolve in creams.

The mixtures of the invention will be administered in the following way. Based upon the tests described in the examples below, the mixtures of the invention prepared from active ingredient(s) in suitable vehicle should be applied as soon as possible after the skin has come into contact with the material(s) that caused the inflammation being treated.

The mixtures of the invention will be applied directly to the area of inflammation to produce a localized effect. Although in salbutamol (discussed above) a systemic effect was noted, none was found in preliminary tests done on the materials used in this invention. It is an advantage to have no systemic effect and to have minimal absorption of these materials.

EXAMPLES

In Examples 1-4, the following types of tests (i.e., models) on animals were used. These were (1) croton oil-induced ear edema in mice, (2) oxazolone-induced ear edema in mice, and (3) UVB-induced erythema in guinea pigs.

EXAMPLE 1

In the croton oil assay, (which is a standard test, which is fully described in Tonelli et al, *Endocrinology*, vol. 77, pp. 625-634, 1965, and which is hereby incorporated herein by reference) topical application of four % croton oil in ethanol (v/v) to the ears of mice causes intercellular edema, vasodilation, and polymorphonuclear leucocyte infiltration into the dermis, leading to an increase over normal ear weight of about 70 to 100%. The inflammatory response is nearly maximal by 6 hours. In the croton oil tests, four volume % croton oil in ethanol was applied to the inner aspect of both ears of each test mouse, and various test materials in vehicle systems were applied to the outer aspect of the ears immediately following croton oil application. Control animals were exposed either to croton oil alone or to croton oil followed by the vehicle alone.

Six hours after exposure to croton oil and/or test material, animals were sacrificed; and punch biopsies of the ears were weighed and compared to the respective vehicle control.

Compounds were tested in simple solutions, including dimethylacetamide/acetone/ethanol (i.e., DMAC/A/E v/v 40/30/30) and N-methyl pyrrolidone/ethanol (NMP/E v/v 50/50). Comparative controls were chosen based on their known activity in each of the three above-described animal assays and included in all three tests (in Examples 1, 2 and 3) hydrocortisone valerate (HCV) in the croton oil and oxazolone assays, indomethacin (which is a potent aspirin-like nonsteroidal anti-inflammatory agent) in the UVB test, and salbutamol (a $\beta_2$ agonist, discussed above in the Background of the Invention).

The percent inhibition of induced mouse ear edema (or erythema) for each of the three models (in Examples 1, 2 and 3) is calculated:

$$\frac{\text{Control Ear Weight} - \text{Test Ear Weight}}{\text{Control Ear Weight}} \times 100.$$

The croton oil assay appeared to be more sensitive to steroidal anti-inflammatory agents than to aspirin-like nonsteroidal anti-inflammatory agents. Unexpectedly, unlike the aspirin-like nonsteroidal anti-inflammatory agents, the $\beta_2$-agonists used in this invention were effective in reducing the croton oil-induced inflammation.

The anti-inflammatory activities of approximately 45 $\beta_2$-adrenergic agonists were evaluated in the croton oil-induced mouse ear edema assay (which produces acute dermatitis); and the more active compounds were subsequently tested in the oxazolone-induced mouse ear edema assay (which produces contact allergic dermatitis) and in the UVB-induced erythema assay in guinea pigs.

Out of the group of approximately 45 compounds which included zinterol and analogs thereof, four compounds (one of which was zinterol) demonstrated high topical cutaneous anti-inflammatory activity in the croton oil assay at 1.6 w/v % (weight/total volume ethanol + test material). These four compounds were subsequently tested topically at other concentrations in the croton oil assay and were also tested topically in the oxazolone assay and in the UVB test. In these subsequent tests, zinterol appeared to be the most consistently active compound.

Given below in Table I are the results of zinterol and the controls salbutamol and HCV, at 1.6 w/v% and 0.2 w/v% in the croton oil assay in each of two solvent systems. Also included in Table I is data for bitolterol, a commercially available $\beta_2$ agonist which has previously been used as an anti-allergy compound but which has not previously been known for utility as topically active against cutaneous inflammations. A direct comparison of bitolterol and zinterol was made. Both exhibited similar topical anti-inflammatory activity.

The results in Table I show that in the croton oil assay, zinterol at 1.6 w/v percent and at 0.2 w/v percent and bitolterol at 1.6 w/v percent all showed good to moderate reductions in ear edema and were equivalent to or slightly less effective than hydrocortisone valerate (i.e., HCV) but were more effective than salbutamol.

EXAMPLE 2

Oxazolone-induced contact sensitization in mice is characterized by edema and cellular infiltration, primarily of the monocyte type, with close to 100% increase in the mouse ear weight. (This model is fully described in N. J. Lowe et al., *British J. of Dermatology*, vol. 96, pp. 433-438, 1977, which is hereby incorporated herein by reference. In this model, test materials were applied topically to the outer aspect of the challenged ear of each test animal immediately following the challenge application of oxazolone to the inner aspect of the ear.

TABLE I

% Inhibition of Croton Oil-Induced Mouse Ear Edema in Two Vehicles[1]

| Compound | In DMAC/Acetone/ETOH[2] | | In NMP/ETOH[3] | |
|---|---|---|---|---|
|  | 1.6 w/v % | 0.2 w/v % | 1.6 w/v % | 0.2 w/v % |
| Zinterol | 69[a], 50[b] | 54[h], 34[i] | 69[m], 63[n] | 92[r], 58[s] |
|  | 81[c], 66[d] | 29[j], 6[k] | 70[o], 48[p] | 56[t], 44[u] |
|  | 63[e], 48[f] | 20[l] | 73[q] | 57[v], 38[x] |
|  | 45[g] |  |  | 34[y], 61[f] |
| Bitolterol |  |  | 61 | 42[x], 25[y] |
|  |  |  |  | 34[z] |
| Salbutamol[4] | 26[a], 0[b] | −34[j*], −45[k] | 54[m], 49[n] |  |
|  |  |  | 23[o], 0[p] |  |
|  |  |  | 37[q] |  |
| HCV | 78[c], 59[d] | 25[j], 38[k] | 70[n], 71[q] | 71[r], 62[s] |
|  | 16[e], 48[f] | 34[l], | | 64[t], 67[u] |
|  | 59[g] |  |  | 73[v] |

[1]Each value is the mean of 10 to 15 animals. Approximately 10 to 35% variability is observed in this test.
[2]Dimethylacetamide/Acetone/Ethanol (v/v, 40/40/30).
[3]N—methyl 2-pyrrolidone/Ethanol (v/v, 50/50).
[4]Tested in Ethanol/H$_2$O (50/50) due to solubility limitations.
[a] to [z]Values with the same alphabetical superscript were observed in the same experiment.
*The minus sign indicates no inhibition, but rather potentiation, of the inflammation.

The animals were sacrificed at 8 or 24 hours after treatment; and punch biopsies of the ears were weighed and compared to controls which were challenged as described above and exposed to the vehicle alone.

The oxazolone assay appeared to be sensitive to steroidal anti-inflammatory drugs and relatively insensitive to nonsteroidal anti-inflammatory drugs. Again, unexpectedly, unlike the aspirin-like nonsteroidals (such as indomethacin), the $\beta_2$-agonists showed topical anti-inflammatory activity.

In Table II, the results of tests on percent of inhibition of oxazolone-induced edema in mouse ears using various concentrations of zinterol, salbutamol, or HCV as active ingredient are given for oxazolone in three solvent systems of DMAC/acetone/ethanol (v/v 40:30:30).

From the results in Table II, in the oxazolone assay, one can observe that zinterol at 3 and 1.6 weight percent showed slight reduction in ear edema with no dose-related effect and was equal to salbutamol but slightly less active than HCV.

Compounds in Tables I and II can be compared directly.

EXAMPLE 3

Another series of tests were run for the sake of completeness, although it was not expected that $\beta_2$-agonists (which are vasodilators) would show results comparable to the aspirin-like non steroidal agents (which are not vasodilators).

TABLE II

| | % Inhibition of Oxazolone-Induced Edema in Mouse Ear[1,2] Concentration | | % Inhibition of Oxazolone-Induced Edema in Mouse Ear[2,3] Concentration | |
|---|---|---|---|---|
| Compound | 0.2 w/v % | 1.6 w/v % | 1.6 w/v % | 3 w/v % |
| Zinterol | 22[a], −17[b] | 48[c], 17[d] | 35[h], 30[i] | 39[l] |
|  |  | 41[e] | 14[j], 43[k] |  |
| Salbutamol | −1[a], −9[b] | 2[c], 0[d], | 21[h], 28[i] | 31[l] |
| HCV | 16[a], 16[b] | 36[c], 27[d] | 38[h], 8[i] | 39[l] |
|  |  |  | 31[j], 42[k] |  |

[1]Above agents tested in DMAC/acetone/ethanol (v/v 40:30:30).
[2]Each value is the mean of 10 to 15 animals. Approximately 20 to 35% variability is observed in this test.
[3]Above agents tested in N—methylpyrrolidone:ethanol (v/v 1:1).
[a] to [l]Values with the same alphabetical superscript were observed in the same experiment.

In the UVB test, cutaneous erythema is induced in guinea pigs. This test is a standard test widely used for testing anti-inflammatory agents and is fully described in K. F. Swingle, "Evaluation for Anti-Inflammatory Activity", in *Anti-Inflammatory Agents*, vol. 2, ed. by Scherrer and Whitehouse, pp. 34-122, London: Academic Press, 1974, hereby incorporated herein by reference. In the UVB model, the test material was applied topically to the irradiated sites immediately following exposure to UVB. Erythema was scored on a 0 to 4 scale, 3 and 6 hours after irradiation.

In Table III, the percent changes in UVB-induced erythema in guinea pigs at 3 and 6 hours after treatment with zinterol are given, along with results of treatment with salbutamol and indomethacin.

As shown by the results in Table III for the UVB assay, zinterol at 3 and 1.6 weight percent showed slight to moderate activity with no consistent dose effect and was highly variable. Similar effects were seen with salbutamol. However, indomethacin at 1 weight percent showed good to very good activity on a consistent basis.

The results given above in Tables I, II and III are summarized below in Table IV.

Based upon the summary in Table IV, one can validly conclude that, at the same concentrations, zinterol appears to be almost as effective as HCV and more effective than salbutamol in the croton oil assay.

TABLE III

% Change in UVB - Induced Erythema in Guinea Pig at 3 and 6 Hours after Treatment[1]

| | Drug Concentration (%)[2] | | | | Drug Concentration (%)[3] | |
|---|---|---|---|---|---|---|
| | 1.6 | | 3 | | 1.6 | 3 |
| | Time (Hr.) | | | | | |
| Compound | 3 | 6 | 3 | 6 | 3 6 | 3 6 |
| Zinterol | 0 | 13 | NT* | | 9  26 | 48  18 |

TABLE III-continued

% Change in UVB - Induced Erythema
in Guinea Pig at 3 and 6 Hours after Treatment[1]

| Compound | Drug Concentration (%)[2] | | | | Drug Concentration (%)[3] | | | |
|---|---|---|---|---|---|---|---|---|
| | 1.6 | | 3 | | 1.6 | | 3 | |
| | Time (Hr.) | | | | | | | |
| | 3 | 6 | 3 | 6 | 3 | 6 | 3 | 6 |
| | 37 | 56 | | | | | 75 | 25 |
| | 9 | 19 | | | | | | |
| | 27 | +9 | | | | | | |
| Salbutamol[4] | 9 | +4 | +39 | +39 | | | 42 | 32 |
| | | | 74 | 71 | | | 45 | 25 |
| Indomethacin | 72 | 43 | | | 100 | 74 | | |
| (1%) | 54 | 48 | | | 93 | 85 | | |
| | 82 | 54 | | | 91 | 87 | | |

[1] All test material applied immediately post-irradiation.
[2] Test material prepared in Dimethyl acetamide/acetone/ethanol (v/v, 40/30/30) and given as w/v %.
[3] Test material prepared in N—methyl 2-pyrrolidone/ethanol (v/v, 50/50) and given as w/v %.
[4] Tested in Ethanol/H2O (50/50) or NMP/H2O (50/50) due to solubility limitations.
*Not tested due to solubility limits at 1.6%.

Therefore, zinterol is a promising candidate for reducing anti-inflammatory activity in humans, based upon the data disclosed above. Zinterol is expected to be devoid of many side effects which are exhibited by the current steroid therapy.

EXAMPLE 4

In further testing, two analogs of zinterol, compounds IV and V, were tested and were found to show anti-inflammatory activity comparable to that of zinterol.

In these tests, the anti-inflammatory effect of these three $\beta_2$ agonists when applied topically to the croton oil-induced ear edema in mice was investigated. In these tests, 50 μl of 4 weight percent croton oil in ethanol was applied to the inner aspects of the right and the left ears of Swiss albino mice, followed immediately by 25 μof suspensions of 0.02, 0.2, and 0.8 weight percent of compound IV and compound V in N-methylpyrrolidone/Ethyl alcohol (i.e., NMP/ETOH) applied to the outer aspect of each ear. Croton oil treated and nontreated control groups were included. These control groups are included in the data as described hereinbefore.

Six hours later, the animals were sacrificed with CO2 gas, and a 5/16 inch punch biopsy of each ear was taken and weighed immediately.

TABLE IV

Topical Anti-Inflammatory Activity of Zinterol in 3 Animal Models
(Salbutamol, HCV and Indomethacin Tested as Comparative Controls)

| | Croton Oil Assay (Edema) | Oxazolone Assay (Edema) | UV-B Assay (Erythema) |
|---|---|---|---|
| Zinterol | +++ | + | + |
| Salbutamol | + | + | + |
| HCV | +++ | + | NT[1] |
| Indomethacin | + | + | +++ |

Anti-Inflammatory Activity and (range of % inhibition)
+ = Slight (30-44), ++ = moderate (45-59) and +++ = high (60%)
[1] NT = Not tested.

The anti-inflammatory effects for the test agents were assessed by a comparison of the biopsy weights of the test and control groups.

The results of three studies for various concentrations of the test material in NMP/ETOH are given below in Table V and show that both compound IV and compound V are comparable to zinterol in reducing the mouse ear edema.

It will be appreciated that the compounds of formula II can be formulated into a wide variety of formulations by standard means well known to those skilled in the art. Such formulations include for example nasal sprays (one spray of which may be prepared, for example, with trichloromonofluoromethane, dichlorodifluoromethane, and oleic acid), rectal suppositories, vaginal suppositories, ointments, creams, gels, and lotions.

TABLE V

% Reduction of Ear Edema Weight as Compared to Control Ears + S.D.

| Concentration (%)* | Test Material | | |
|---|---|---|---|
| | Compound IV | Compound V | Zinterol |
| 0.02 | 10.6 | 29.9 | 14.2 |
| | 25.6 | | 23.6 |
| Mean ± S.D. | 18.1 ± 10.6 | | 18.9 ± 6.6 |
| 0.2 | 32.9 | 53.5 | 39.5 |
| | 48.7 | | 66.2 |
| | 49.4 | | 46.6 |
| Mean ± S.D. | 43.7 ± 9.3 | | 50.8 ± 13.8 |
| 0.8 | 61.6 | 69.9 | 68.2 |
| | 53.4 | | 56.6 |
| Mean ± S.D. | 57.5 ± 5.8 | | 62.4 ± 8.2 |

*Weight/Volume
Data given on the same line in Tables III and V were obtained in the same experiment, and therefore a direct comparison is shown.

What is claimed is:

1. A method of reducing topical inflammation in a mammal in need thereof which comprises topically administering to said mammal an amount effective to produce a topical anti-inflammatory effect of a composition comprising (a) a compound of the formula

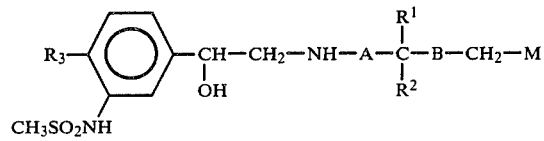

wherein $R^1$ and $R^2$ are independently hydrogen or (lower)alkyl, provided that $R^1$ and $R^2$ cannot both be hydrogen; wherein M is phenyl, indole or hydrogen; wherein A is $(-CH_2-)_n$ in which n is 0, 1 or 2; wherein B is $(-CH_2-)_m$ in which m is 0, 1 or 2; and wherein $R^3$ is

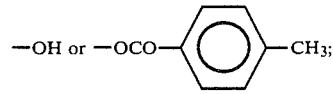

and (b) a compatible, topically acceptable vehicle.

2. A method according to claim 1 wherein m and n are both zero and $R^3$ is —OH.

3. A method according to claim 2 wherein M is phenyl and $R^1$ and $R^2$ are both methyl.

4. A method according to claim 2 wherein M is indole and $R^1$ and $R^2$ are both methyl.

5. A method according to claim 2 wherein $R^1$ is methyl, $R^2$ is hydrogen and M is indole.

6. A method according to claim 1 wherein m and n are both zero, $R^3$ is

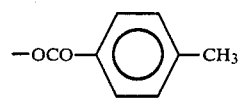
and M is hydrogen.
7. A method of claim 2 wherein said composition is in the form of a cream, lotion or gel.
8. A method of claim 2 wherein said composition is a spray formulation.
9. A method of claim 2 wherein said composition is a suppository formulation.
* * * * *